(12) United States Patent
Damren et al.

(10) Patent No.: US 10,221,383 B2
(45) Date of Patent: Mar. 5, 2019

(54) DISPOSABLE BIOREACTOR CONDENSER BAG AND FILTER HEATER

(71) Applicant: GE HEALTHCARE BIO-SCIENCES CORP., Piscataway, NJ (US)

(72) Inventors: Richard Damren, Marlborough, MA (US); Colin Touhey, Medway, MA (US); Thomas Erdenberger, Arlington, MA (US); Michael Fisher, Woodstock, CT (US); Geoffrey Hodge, Sutton, MA (US); Patrick Guertin, Mendon, MA (US); Parrish Galliher, Littleton, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 183 days.

(21) Appl. No.: 15/259,338

(22) Filed: Sep. 8, 2016

(65) Prior Publication Data

US 2016/0376539 A1     Dec. 29, 2016

Related U.S. Application Data

(63) Continuation of application No. 13/434,345, filed on Mar. 29, 2012, now Pat. No. 9,499,781, and a
(Continued)

(51) Int. Cl.
*F25B 21/02*     (2006.01)
*C12M 1/00*      (2006.01)
(Continued)

(52) U.S. Cl.
CPC ........... *C12M 29/26* (2013.01); *B01D 5/0042* (2013.01); *B01D 5/0093* (2013.01);
(Continued)

(58) Field of Classification Search
CPC ...... C12M 29/26; C12M 29/04; C12M 41/12; C12M 41/18; C12M 41/22; C12M 23/28;
(Continued)

(56) References Cited

U.S. PATENT DOCUMENTS 3,212,274 A * 10/1965 Eidus ...................... F25B 21/04
                                                       165/110
3,867,260 A *  2/1975 Freedman ............ B01D 5/0003
                                                       165/104.25
(Continued)

FOREIGN PATENT DOCUMENTS

DE         202009006839      *  8/2009

*Primary Examiner* — Joseph F Trpisovsky
(74) *Attorney, Agent, or Firm* — Grogan, Tuccillo & Vanderleeden, LLP

(57) ABSTRACT

A system for condensing moisture in a moist gas stream entering or leaving a bioreactor includes a condenser container, the condenser container comprising: an outer wall surface and an inner wall surface, the inner wall surface defining an interior chamber for holding a fluid; and a first fitment attached to the outer wall surface and forming a first port configured to allow the moist gas stream to flow into the interior chamber; a second fitment attached to the outer wall surface and forming a second port configured to allow a dried gas to flow from the interior chamber and out of the second port; and a cooling device in contact with at least one portion of the outer wall surface and arranged to cool the at least one portion of the outer wall surface.

19 Claims, 2 Drawing Sheets

Related U.S. Application Data continuation of application No. PCT/US2010/050859, filed on Sep. 30, 2010.

(60) Provisional application No. 61/247,368, filed on Sep. 30, 2009.

(51) Int. Cl.
    *B01D 5/00* (2006.01)
    *B01D 46/42* (2006.01)
    *B01D 53/26* (2006.01)
    *C12M 1/34* (2006.01)

(52) U.S. Cl.
    CPC ....... *B01D 46/4263* (2013.01); *B01D 53/265* (2013.01); *C12M 23/28* (2013.01); *C12M 29/04* (2013.01); *C12M 41/12* (2013.01)

(58) Field of Classification Search
    CPC ...... C12M 23/04; C12M 23/14; C12M 23/26; B01D 5/0003; B01D 5/0015; B01D 5/0081; B01D 5/009; B01D 5/0042; B01D 5/0093; B01D 53/265; B01D 46/4263; B01D 5/00; B01D 8/00; B01D 47/05; F28F 2255/02; F28F 3/12; F28F 21/06
    USPC ......... 62/3.2, 3.4, 3.5, 93, 283, 315; 165/46, 165/84, 104.15, 104.16, 104.19, 169, 170, 165/185
    See application file for complete search history.

(56) References Cited

U.S. PATENT DOCUMENTS

| | | | |
|---|---|---|---|
| 5,512,141 A * | 4/1996 | Koistinen | B01D 1/007 159/13.1 |
| 8,455,242 B2 | 6/2013 | Staheli et al. | |
| 9,127,246 B2 | 9/2015 | Staheli et al. | |
| 9,284,524 B2 | 3/2016 | Staheli et al. | |
| 2005/0272146 A1* | 12/2005 | Hodge | B01F 13/0827 435/289.1 |
| 2008/0262409 A1* | 10/2008 | Derrico | A61M 5/44 604/19 |
| 2011/0076759 A1* | 3/2011 | Reif | C12M 21/04 435/297.1 |

* cited by examiner

DISPOSABLE BIOREACTOR CONDENSER BAG AND FILTER HEATER

RELATED APPLICATIONS

This application is a continuation of U.S. application Ser. No. 13/434,345, which is a continuation of International Application No. PCT/US2010/050859, which designated the United States and was filed on Sep. 30, 2010, published in English, which claims priority to U.S. Provisional Patent Application No. 61/247,368, filed on Sep. 30, 2009. The entire teachings of the above applications are incorporated herein by reference.

FIELD OF INVENTION

The present disclosure relates to devices and methods for the use with disposable bioreactors or with non-disposable tank bioreactors.

BACKGROUND

Cell culturing is an essential step in manufacturing biological products, and may be carried out in disposable bioreactors systems or in non-disposable bioreactors such as steel tank vessels. Oxygen is continuously supplied to promote cell growth, and carbon dioxide is removed. A gas stream going to or coming from a bioreactor may contain moisture entrained within the gas stream. The moisture in the gas may condense as the gas passes through a filter or other system component. The moisture and/or condensation may be detrimental to the functioning of the filter or other system component.

A number of yet un-solved problems are inherent in currently available condenser designs for use with bioreactors. Some prior art designs incorporate several functionally different areas such as, for example, subducts and different cooling and heating zones, that result in a complex and costly assembly requiring special tooling, specially molded or machined components. Prior art designs also separate a vessel for condensate collection from the heat exchange area, thus adding complexity to the part instead of integrating condensate removal directly from the heat exchange zone. Because prior art designs are complex and tend to be expensive, such condensers are not truly disposable.

Another yet un-resolved problem inherent in many prior art condenser designs is that the heat is removed from the exhaust gas and then the heat is just wasted by pouring it into the environment to get rid of it.

Currently available condensers also may have another drawback inherent in the use of a multiplicity of ducts. Although the relatively long pathway provided by the many ducts increases the surface area of the condenser available for cooling, the decrease in cross-sectional area of a duct also increases the velocity of the gas flowing through the condenser, which in turn decreases the residence time of the exhaust gases in the condenser. The decreased residence time in the condenser results in a decrease in the overall cooling effect of the condenser on the exhaust gas within the condenser bag.

Yet another drawback of many currently available condensers is related to the inclusion of both a cooling zone and a heating zone within the condenser unit. Coupling the condensing function of the unit with a heating function within the same assembly reduces the flexibility of allowing the two functions to be manipulated independently of each other.

Thus, there is an on-going need for an improved apparatus, in particular, a truly disposable apparatus, and method that provide a means to reduce the moisture content of a moist gas within a bioreactor system before it is passed on to a filter or other system component where moisture and/or condensation on the filter or system component may interfere with the functioning of the filter or other system component.

BRIEF SUMMARY OF THE DISCLOSURE

The inventors of the present subject matter have now discovered a disposable bioreactor condenser that overcomes many of the problems found in the use of prior art condensers. The invention inter alia includes the following, alone or in combination. In one aspect, the present invention relates to our discovery of an apparatus and a corresponding method for condensing the water vapor in a stream of gas passing into or out of a bioreactor.

One embodiment of the invention is a system for condensing moisture in a moist gas stream entering a bioreactor or leaving a bioreactor, the system comprising: a condenser container capable of holding a fluid, the condenser container comprising: an outer wall surface and an inner wall surface, the inner wall surface defining an interior chamber for holding the fluid; and a first fitment attached to the outer wall surface of the condenser container, the first fitment forming a first port configured to allow the moist gas stream to flow through the first port and into the interior chamber; a second fitment attached to the outer wall surface of the condenser container, the second fitment forming a second port configured to allow a dried gas to flow from the interior chamber and out of the second port; and a cooling device in contact with at least one portion of the outer wall surface of the condenser container and arranged to cool the at least one portion of the outer wall surface of the condenser container, thereby to condense moisture in the moist gas stream and form a dry gas stream for entering or leaving the bioreactor.

Another embodiment of the invention is a method of condensing moisture in a moist gas stream leaving a bioreactor, the method comprising: providing a system as disclosed in the preceding paragraph; providing fluid communication of the first port of the condenser container with or between a port of the bioreactor arranged to allow the moist gas stream to leave the bioreactor; allowing the moist gas stream leaving the bioreactor to flow through the first port and into the interior chamber of the condenser container; cooling the at least one portion of the outer wall surface of the condenser container; allowing heat to be transferred from the interior chamber of the condenser container to the cooling device, thereby lowering the temperature of the interior chamber of the condenser container; condensing moisture in the moist gas stream; and forming a dry gas stream leaving the bioreactor.

A gas stream leaving a bioreactor typically is passed through a filter. A moist gas would clog the filter. The dry gas stream formed according to an embodiment of the invention will not tend to clog the filter.

In one embodiment, the condensate can be collected and either returned to the bioreactor, sent to another device, or discarded. For example, in one embodiment, the condenser container in the disclosed system for condensing moisture in a moist gas stream may comprise a fitting 50 such as a hose barb for attaching and securing tubing to collect condensate for either a gravity flow of the condensate or a pumping of the condensate from the interior chamber and back into the bioreactor.

Another embodiment of the invention is a method of condensing moisture in a moist gas stream to form a dry gas for addition to a bioreactor, the method comprising:

providing a system as described herein, for example as in paragraph 0009; providing fluid communication of the first port of the condenser container with the moist gas stream; allowing the moist gas stream to flow through the first port and into the interior chamber of the condenser container; cooling the at least one portion of the outer wall surface of the condenser container; allowing heat to be transferred from the interior chamber of the condenser container to the cooling device, thereby lowering the temperature of the interior chamber of the condenser container; condensing moisture in the moist gas stream; thereby forming a dry gas.

The dry gas formed by the disclosed method can then be flowed out of the second port and into a bioreactor.

The cooling device may also include a heating source arranged to provide heating of a filter within the bioreactor. The cooling device may include a thermoelectric module such as, for example, a Peltier heating and cooling module.

BRIEF DESCRIPTION OF THE DRAWINGS

The foregoing and other features and advantages of the invention will be apparent from the following more particular description of illustrative embodiments of the invention, as illustrated in the accompanying drawings. The drawings are not necessarily to scale, emphasis being placed upon illustrating the results of exemplary embodiments of the disclosed apparatus.

DETAILED DESCRIPTION

Figure 1A:
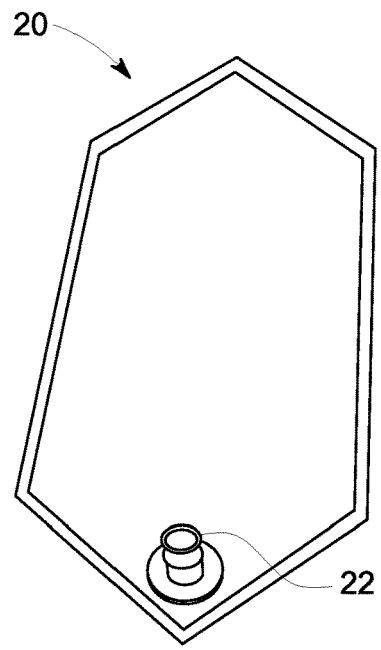
FIG. 1A is a schematic drawing of a perspective view of a prototype two-dimensional disposable bioreactor condenser bag according to an embodiment of the invention.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The invention relates to a system that performs at least one specific function for a bioreactor. The function may be condensing moisture within a gas stream entering or leaving the bioreactor, or it may be heating a filter to prevent condensation within the filter.

We have now discovered a condenser system that utilizes a cooling device to power a disposable bioreactor condenser. The disclosed system may include a filter heater that utilizes heat from a thermoelectric heating and cooling system. Any cooling device could be used in an embodiment of the invention. In a preferred embodiment, the cooling device is a thermoelectric cooling device. A thermoelectric cooling device includes a solid-state method of heat transfer through dissimilar semiconductor materials. Thermoelectric cooling is referred to as "the Peltier Effect," after Peltier, an experimental physicist who discovered the phenomenon in 1834. If a current is passed through a thermocouple, heat is absorbed (or removed) at one junction and is evolved at the other junction of the thermocouple. If the first junction is in a closed region, the first region will be cooled.

We used a thermoelectric Peltier module (TE Technology, Inc., Traverse City, Mich.) to power a disposable bioreactor condenser and filter heater. In general, a thermoelectric Peltier module operates to cool one surface of the module, and the heat removed from the cooled side is transferred to the other hot side of the thermoelectric module. In an embodiment of this invention both the heated side and the cooled side of the thermoelectric Peltier module are used. The cooled side of the Peltier module provides the cooling for the condenser function of the invention, while the heated side of the Peltier module can be used to assist in heating of a filter. In most commonly seen applications using a thermoelectric Peltier cooling module, the heat generated on the heated side of the thermoelectric Peltier module is conducted away from the system as waste heat and is not used. With a slight modification of the disclosed system, that heat can be used for heating a filter. Heating the filter tends to convert any condensed water droplets into the vapor phase so that the condensate does not clog the filter.

In one embodiment of the invention, the condenser container is a single use, flexible, nonporous bag comprising a flexible polyethylene material or film. The condenser container in most of the embodiments described herein is referred to as a "bag" or a "condenser bag" or a "flexible bag." However, other embodiments of the invention may include a rigid or a semi-rigid container instead of a flexible bag. The condenser bag may comprise two sides as in what is known as a "two-dimensional bag," or it may be a three-dimensional bag or have any other suitable shape and size.

The condenser bag may have fitments attached to it. The term "fitment" as used herein refers to a separate object that is heat-welded to the flexible bag film in order to attach it. As such, a fitment often comprises a polymeric material which can be the same or similar to the polymeric material comprising the wall of the flexible bag. A fitment is often a more dense material than the wall of the flexible bag, and may be added to the bag to enable a functionality. A non-limiting example of a fitment is one that forms a port. In one embodiment of the invention, a port is added to the wall of the condenser bag in order to allow gas to enter. In another embodiment of the invention, a port is added to the wall of the condenser bag to allow gas to leave the condenser bag.

In one embodiment of the invention the condenser bag comprises a nonporous polymeric material that is biocompatible with the cells and medium used for cell growth in a bioreactor. FIG. 1A is a schematic drawing of a perspective view of a prototype disposable bioreactor condenser bag 20 according to an embodiment of the invention. The prototype condenser bag 20 is shown with one fitment 22 for a port. A condenser bag according to an embodiment of the invention can have a plurality of fitments and ports. The embodiment depicted in FIG. 1A does not have any structure within the bag to promote turbulence or condensation.

Figure 1B:
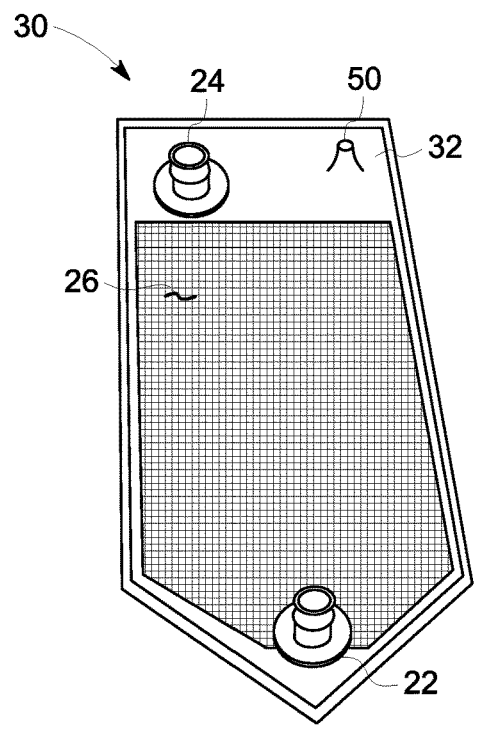
FIG. 1B is a schematic drawing of a perspective view of a two-dimensional disposable bioreactor condenser bag according to an embodiment of the invention, having mesh disposed within the condenser bag and visible through the bag film.

FIG. 1B is a schematic drawing of a perspective view of a disposable bioreactor condenser bag 30 according to an embodiment of the invention. The mesh 26 disposed within the condenser bag 30 is visible through the top surface 32 of the bag film. Two fitments 22, 24 are shown on the outer wall of condenser bag 30. In one embodiment of the invention, fitment 22 is used for forming an inlet port for moist gas and fitment 24 is used for forming an outlet port for dried gas. In another embodiment, fitment 22 can be used to form an outlet and fitment 24 an inlet. In one embodiment the condenser bag 30 is disposable.

The condenser bag 30 is used in conjunction with a cooling source to lower the temperature of a moist gas stream going to or coming from a bioreactor such that condensation of moisture entrained within the gas occurs within the condenser bag 30. This condenser bag 30 can be used to reduce the moisture content of the moist gas before it is passed on to a filter or other system component where moisture and/or condensation may be detrimental to the functioning of the filter or other system component.

In one embodiment, the disposable condenser bag 30 forms a closed volume that has at least one inlet fitment 22 to allow for a moist gas to be flowed into the condenser bag 30 from a bioreactor or from another gas source, and at least one outlet fitment 24 to allow for the passage of the dry gas stream out of the condenser bag 30. The condenser bag 30 may include an internal arrangement of a biocompatible material such as mesh 26 within the closed volume that will promote the condensation of moisture from the gas passing through the condenser bag 30, and also increase the turbulence within the gas stream as it passes through the condenser bag. In one embodiment of the invention, the mesh 26 or other biocompatible material is pleated to provide increased contact of the moist gas stream with the mesh such that it substantially completely fills the gap between the two inner layers of the condenser bag 30.

In another embodiment of the invention, the structure arranged to allow condensation to form thereon, and/or to increase turbulence is a series of fins attached to a support. In yet another embodiment the structure arranged to allow condensation to form thereon comprises a spiral coil. Any structure within the bag that can promote turbulence and/or promote condensation is within the scope of the invention.

Non-limiting examples of materials suitable for forming the structure for promoting condensation within the condenser bag 30 include polyethylene, polypropylene, polyester, polyamide, and a metal.

At least one surface of the condenser bag 30 is in contact with an external cooling source, for example, a cold plate, which by conduction cools at least one surface, for example top surface 32 of the condenser bag 30, which in turn cools the inside surface of the bag 30 and cools the moist gas stream to or below its dew point temperature as the gas flows over the cooled surface.

Figure 2:
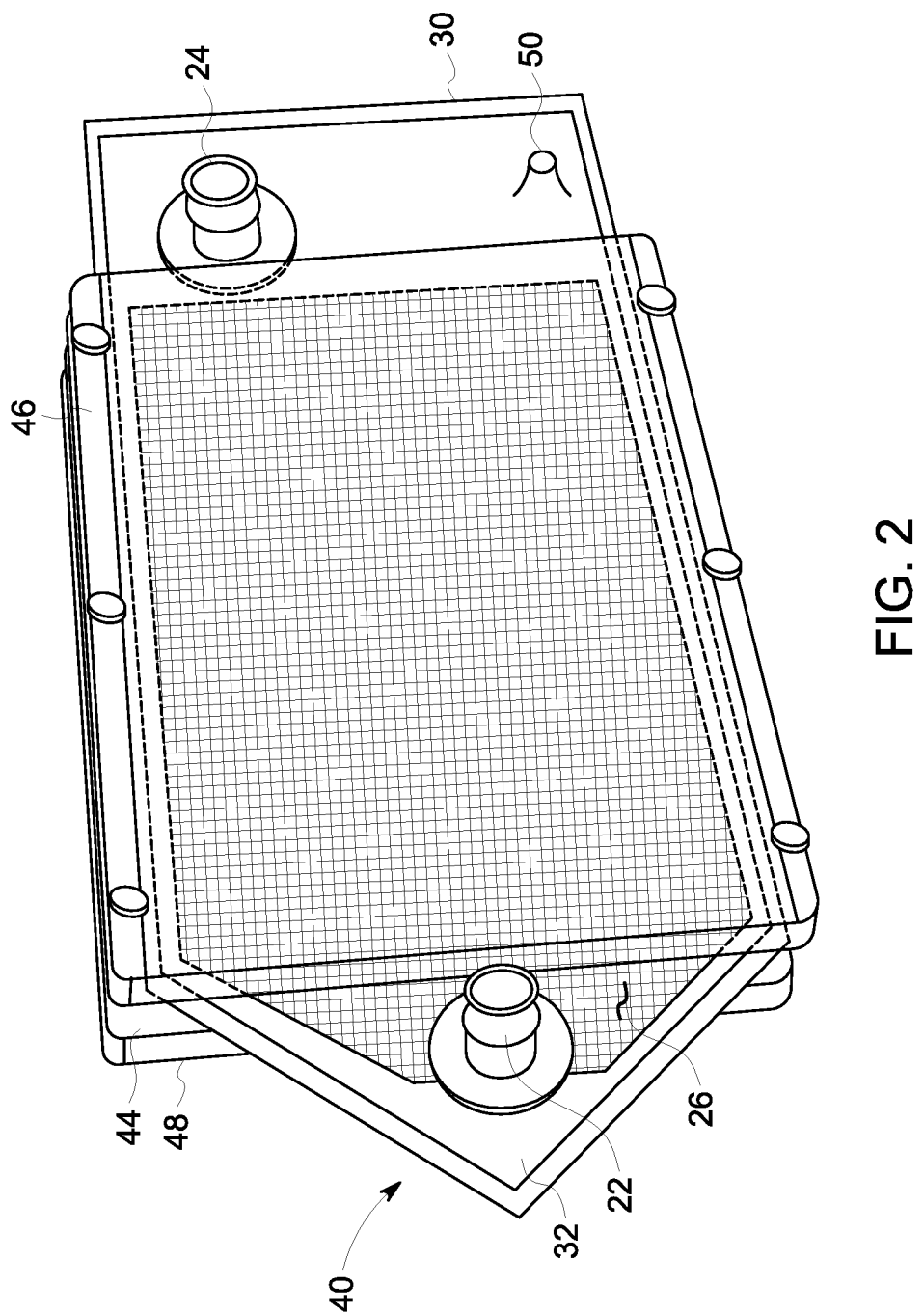
FIG. 2 is a schematic drawing of a perspective view of a system according to an embodiment of the invention, the system utilizing a thermoelectric heating and cooling device for condensing moisture in a gas stream entering or leaving a two-dimensional bioreactor.

FIG. 2 is a schematic drawing of a perspective view of a system 40 according to an embodiment of the invention for condensing moisture in a gas stream entering or leaving a bioreactor. The disposable bioreactor condenser system 40, which may include a filter heater system according to an embodiment of the invention, comprises several major functional components. The components of the system include the disposable bioreactor condenser bag 30, a cold plate, a thermoelectric Peltier module with associated controller, a cold plate/condenser bag holder or frame 46, 48, and a filter heater enclosure (not shown).

In FIG. 2, the system 40 as shown includes a condenser bag front frame holder 46 and a condenser bag back frame holder 48, the frame forming a sandwich with the condenser bag 30 held firmly against a cold plate. The cold plate (not shown) is positioned on surface 44 of the back frame holder 48.

In a preferred embodiment, a cold plate appropriately sized to approximately match the surface area of one side of the condenser bag 30 is attached to the cold side of the thermoelectric Peltier module to maximize its contact area with the disposable condenser bag. In one embodiment of the invention, provision is made on the cold plate to provide a means of securing the disposable condenser bag 30 in position on the cold plate in order to ensure that at least one surface of the disposable condenser bag 30 is in contact with the cold plate surface.

The condensate generated within the condenser bag 30 can be drained from the bag continually or periodically. The condensate that collects within the condenser bag 30 may be drained through an inlet port fitment 22. Alternatively, there may be a separate fitment, for example, a hose barb (not shown) attached to a surface of the condenser bag specifically for draining the condensate. The hose barb may be used for attaching and securing tubing to collect condensate for either a gravity flow of the condensate or a pumping of the condensate from the interior chamber of the condenser bag and back into the bioreactor. This recycling of the liquid water may be utilized to maintain constant volume of the liquid and constant osmolarity within the bioreactor.

Alternatively, the condensate may be sent to another storage device as required by the bioreactor process being used or it may be discarded.

The hot side of the thermoelectric Peltier module generates heat that can provide or assist in the heating of a filter to keep its temperature above the dew point temperature of the gas that is flowing through the filter. With no more than routine experimentation, a suitable enclosure or ducting structure can be devised and attached to the hot side of the thermoelectric Peltier module to allow the heat generated to be directed to the filter in such a manner as to heat or assist in the heating of the filter. The heat may be actively directed to the filter by use of a fan or may be passively directed to the filter using convection, or a suitable combination of the two methods may be used.

The relatively large cross-sectional area of a condenser bag according to an embodiment of the disclosed invention increases the residence time of the moist gas within the condenser container as compared to the residence time of a moist gas in a prior art system using a pathway of ducts. This is because the velocity of the gas stream is increased in a narrowed passageway such as a long duct. By including a mesh or other biocompatible material inside the large cross sectional area of the bag to enhance condensation, we achieved similar or improved results at a much lower cost than that of a system with extensive ductwork.

The mesh or screen material in a condenser bag according to an embodiment of the invention serves several functions. First, the mesh increases turbulent flow within the bag which ensures that the moist gas comes into contact with the cooled sidewalls of the condenser bag at some point in its passage through the condenser bag, instead of just flowing straight through the center of the condenser bag. Secondly, after the condenser bag has been operating for a short period of time, cooled condensate droplets become trapped on the screen material and these droplets will assist in causing even more moisture to condense out of the moist gas. The mesh helps increase the surface area on which condensation can occur.

Prior art condensers generally include both a cooling zone and a heating zone within the condenser unit. That coupling of the condensing function of the unit with a heating function within the same assembly reduces the flexibility of allowing the two functions to be manipulated independently of each other. Prior art condensers generally remove heat from the exhaust gas and then just allow the heat to dissipate into the environment.

In the disclosed condenser bag, those two functions, cooling and heating, are separate. The heating zone is not a part of the disclosed condenser bag. A disclosed embodiment includes the concept, for example, of taking the heat that is removed from the exhaust gas and using it to heat another component, such as the exhaust filter.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawing), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EQUIVALENTS

While this invention has been particularly shown and described with references to preferred embodiments thereof, it will be understood by those skilled in the art that various changes in form and details may be made therein without departing from the scope of the invention encompassed by the appended claims.

We claim:

1. A system for condensing moisture in a moist gas stream entering or leaving a bioreactor, the system comprising:
a flexible bag capable of receiving the moist gas stream, the flexible bag having an outer wall surface and an inner wall surface, the inner wall surface defining an interior chamber for receiving the moist gas stream;
a cooling device having a cold plate, the cold plate being in contact with at least one portion of the outer wall surface of the flexible bag and arranged to cool the at least one portion of the outer wall surface, thereby condensing moisture in the moist gas stream entering or leaving the bioreactor; and
a counterplate;
wherein at least a portion of the flexible bag is positioned between the counterplate and the cold plate.

2. The system of claim 1, wherein:
the cold plate is sized to approximately match the surface area of one side of the outer wall surface of the flexible bag.

3. The system of claim 1, wherein:
a majority of the outer wall of the flexible bag is sandwiched between the cold plate and the counterplate.

4. The system of claim 1, wherein:
the flexible bag includes a first fitment attached to the bag, the first fitment forming a first port configured to allow the moist gas stream to flow through the first port and into the interior chamber, and a second fitment attached to the bag, the second fitment forming a second port configured to allow a dried gas to flow from the interior chamber and out of the second port.

5. The system of claim 4, wherein:
the flexible bag includes a third port for draining the moisture from a lower end of the flexible bag during use.

6. The system of claim 4, wherein:
the first fitment is arranged perpendicular to the outer wall surface of the bag and to a gas flowpath within the bag so that the moist gas stream enters the interior chamber of the bag through the first port in a direction perpendicular to the outer wall surface of the bag and to the gas flowpath within the bag.

7. The system of claim 1, wherein the cooling device is configured to provide cooling for the at least one portion of the outer wall surface of the flexible bag.

8. A method of processing a gas stream, the method comprising:
passing a moist gas stream into an interior chamber of a two-dimensional flexible condenser bag formed from a polymeric material;
cooling the moist gas stream within the condenser bag so as to separate the moist gas stream within the condenser bag into a condensate and a dry gas; and
removing the condensate and the dry gas from the condenser bag, the dry gas being removed by passing the dry gas through a heated filter;
wherein passing the moist gas stream into the interior chamber includes passing the moist gas stream into the interior chamber in a direction perpendicular to an outer wall surface of the flexible condenser bag and to the gas flowpath within the condenser bag.

9. The method according to claim 8, wherein:
the moist gas stream is passed into the condenser bag from a bioreactor in which cells are being grown.

10. The method according to claim 8, wherein:
removing the condensate from the condenser bag includes draining the condensate from a lower end of the condenser bag.

11. A method of processing a gas stream, the method comprising:
passing a moist gas stream into an interior chamber of a two-dimensional flexible condenser bag formed from a polymeric material;
cooling the moist gas stream within the condenser bag so as to separate the moist gas stream within the condenser bag into a condensate and a dry gas; and
removing the condensate and the dry gas from the condenser bag, the dry gas being removed by passing the dry gas through a heated filter; and
positioning at least a portion of the condenser bag between a cold plate of a cooling device and a counterplate such that the cold plate is arranged to cool at least one portion of an outer wall surface of the condenser bag.

12. The method according to claim 11, wherein:
the cold plate is sized to approximately match the surface area of one side of the outer wall surface of the flexible bag.

13. A method for processing a moist gas stream, the method comprising:
positioning a flexible condenser bag between a cooling plate and a counter plate so that said cooling plate contacts an outer wall surface of said flexible condenser bag;
supplying a gas to a fluid within a container so that the gas passes through the fluid to form a moist gas stream within the container;
passing the moist gas stream out of the container and into the flexible condenser bag;
cooling the moist gas stream within the condenser bag so as to separate the moist gas stream within the condenser bag into a condensate and a dry gas; and
removing the condensate and the dry gas from the condenser bag.

14. The method according to claim 13, wherein:
the flexible condenser bag is formed from a polymeric material.

15. The method according to claim 13, further comprising:
returning the condensate back into the container.

16. The method according to claim 13, further comprising:
passing the dry gas removed from the condenser bag through a filter.

17. The method according to claim 13, wherein:
removing the condensate from the condenser bag includes draining the condensate from a lower end of the condenser bag.

18. The method according to claim 13, wherein:
passing the moist gas stream into the condenser bag includes passing the moist gas stream into the condenser bag in a direction perpendicular to an outer wall surface of the condenser bag and to the gas flowpath within the condenser bag.

19. A method for processing a moist gas stream, the method comprising:
supplying a gas to a fluid within a container so that the gas passes through the fluid to form a moist gas stream within the container;
passing the moist gas stream out of the container and into a two-dimensional flexible condenser bag placed in close association with a cold plate of a cooling device, the cold plate configured to cool at least one portion of an outer wall surface of the flexible condenser bag;
cooling the moist gas stream within the condenser bag so as to separate the moist gas stream within the condenser bag into a condensate and a dry gas; and
removing the condensate and the dry gas from the condenser bag.

* * * * *

UNITED STATES PATENT AND TRADEMARK OFFICE
CERTIFICATE OF CORRECTION

| | |
|---|---|
| PATENT NO. | : 10,221,383 B2 |
| APPLICATION NO. | : 15/259338 |
| DATED | : March 5, 2019 |
| INVENTOR(S) | : Richard Damren et al. |

It is certified that error appears in the above-identified patent and that said Letters Patent is hereby corrected as shown below:

On the Title Page

Item (72) reads:
"COLIN TOUHEY"
Should read:
--COLIN TUOHEY--

Item (71) reads:
"Piscataway, NJ"
Should read:
--Marlborough, MA--

Signed and Sealed this
Twenty-fifth Day of June, 2019

Andrei Iancu
*Director of the United States Patent and Trademark Office*